United States Patent [19]

Pallucca

[11] 4,440,962
[45] Apr. 3, 1984

[54] PROCESS FOR REMOVING NITROSATING AGENTS FROM 1-CHLORO-2,6-DINITRO-4-(TRI-FLUOROMETHYL) BENZENE

[75] Inventor: Edoardo Pallucca, Settimo Milanese, Italy

[73] Assignee: Oxon Italia S.P.A., Milan, Italy

[21] Appl. No.: 370,746

[22] Filed: Apr. 22, 1982

[51] Int. Cl.$^3$ .............................................. C07C 79/12
[52] U.S. Cl. ................................................... 568/933
[58] Field of Search ........................ 568/933, 934, 935

[56] References Cited

U.S. PATENT DOCUMENTS 4,120,905 10/1978 Cannon et al. ...................... 568/933
4,128,425 12/1978 Greenwald ........................... 430/239
4,338,473  7/1982 Habig et al. ......................... 568/933

*Primary Examiner*—Leland A. Sebastian
*Attorney, Agent, or Firm*—Young & Thompson

[57] ABSTRACT

To obtain technical TRIFLURALIN with a nitrosoamine content not exceeding 1 ppm, for use as a herbicide, 1-chloro-2,6-dinitro-4-(trifluoromethyl) benzene (DINITRO-PCBT) is freed from nitrosating agents by a process in which DINITRO-PCBT is treated with an aqueous bisulphite solution having an $SO_2$ concentration of between 1% and 5% at a pH of between 1 and 3, at a temperature of between 50° and 100° C. for a time of between 1 and 3 hours. The organic layer is then separated from the aqueous layer, and the acidity and last traces of the bisulphite solution are eliminated from the organic layer by means of an aqueous alkaline solution.

9 Claims, No Drawings

PROCESS FOR REMOVING NITROSATING AGENTS FROM 1-CHLORO-2,6-DINITRO-4-(TRIFLUOROMETHYL) BENZENE

BACKGROUND OF THE INVENTION

This invention relates to a process for removing nitrosating agents from 1-chloro-2,6-dinitro-4-(trifluoromethyl)benzene, from which it is possible to obtain technical TRIFLURALIN with a particularly low nitrosoamine content (specifically NDPA).

It is well known that certain agricultural products can contain nitrosoamines, and the danger of these substances is equally well known.

In particular, it has been public knowledge since 1976 that nitrosoamines are present in formulations of agricultural products such as TRIFLURALIN

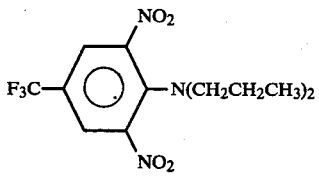

which is a very important selective herbicide, and is prepared by the following reaction

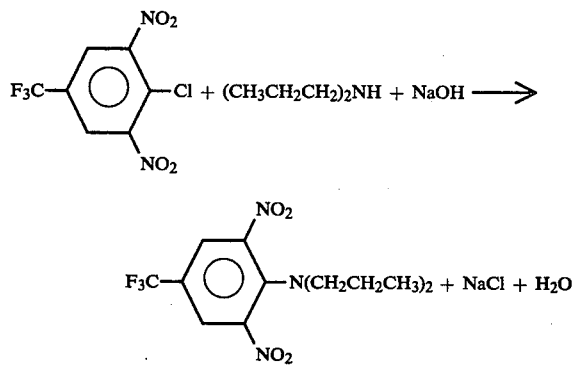

This compound contains N-nitrosodipropylamine (NDPA), i.e. $(CH_3CH_2CH_2)_2N-NO$ as impurity, this forming during the herbicide synthesis.

This is because 1-chloro-2,6-dinitro-4-(trifluoromethyl)benzene (DINITRO-PCBT), which is prepared by dinitrating 1-chloro-4-(trifluoromethyl)benzene (PCBT), and which is the starting substance for synthesising TRIFLURALIN, contains dissolved nitrogen oxides of various composition, which are responsible for the formation of nitrosoamines in accordance with the reaction
$(CH_3CH_2CH_2)_2NH + (NO)_x \rightarrow (CH_3CH_2CH_2)N-NO$
which takes place in a basic environment.

As stated, the danger of nitrosoamines is well known. They exercise an acute hepatotoxic action, and in particular are carcinogenic, mutagenic and teratogenic. It is therefore essential that the quantity of NDPA in the TRIFLURALIN is as low as possible, and legislation in the more advanced countries considers that an NDPA content in the technical product of less than 1 ppm is acceptable.

From research carried out up to the present time, it has emerged that if the DINITRO-PCBT is synthesised without special purification processes, the quantity of dissolved nitrogen oxides is such as to generate an NDPA content of between 150 and 500 ppm in the technical TRIFLURALIN subsequently produced. If purification processes are introduced (for example those indicated in U.S. Pat. No. 4,120,905), the nitrosating agents contained in the DINITRO-PCBT are reduced, but the results obtained are not constant and it is not possible to obtain technical TRIFLURALIN with an NDPA content of less than 1 ppm.

Research has therefore been directed towards methods which provide for eliminating the formed nitrosoamines from the final product.

Even if they allow a final product of satisfactory characteristics to be obtained, processes which comprise the destruction of preformed nitrosoamines have the very serious drawback of being dangerous because of the presence of nitrosoamines in certain stages of the process during which contact, including accidental contact, is always possible with the environment and with the process operators.

It has therefore appeared very desirable to discover processes which exclude the formation of nitrosoamines in order to use them in place of processes which destroy the already formed nitrosoamines, and the research of the applicant has developed in this direction.

This research has been successful, and the present invention relates to a novel purification process for obtaining DINITRO-PCBT practically free from nitrosating agents, to which said research has led. As will be apparent hereinafter, using the DINITRO-PCBT obtained by this process it is possible to prepare technical TRIFLURALIN with an NDPA content which is always less than 1 ppm. Thus the stated object is completely attained.

SUMMARY OF THE INVENTION

The present invention therefore relates to a process for obtaining 1-chloro-2,6-dinitro-4-(trifluoromethyl)-benzene (DINITRO-PCBT) free from nitrosating agents, characterised in that DINITRO-PCBT is treated with an aqueous bisulphite solution having an $SO_2$ concentration of between 1% and 5% at a pH of between 1 and 3, at a temperature of between 50° and 100° C. for a time of between 1 and 3 hours, and in that the organic layer is separated from the aqueous layer, and the acidity and last traces of the bisulphite solution are eliminated from the organic layer by an aqueous alkaline solution.

The bisulphite used is preferably sodium bisulphite, but analogous results can be obtained by using other bisulphites such as potassium bisulphite or ammonium bisulphite. Alternatively, the bisulphite can be prepared directly in the reactor by reacting $SO_2$ with the necessary quantity of alkali. As stated, the $SO_2$ concentration of the bisulphite solution is between 1% and 5%. Preferably, a concentration of 1.6% is used. Concentrations higher than 5% should be avoided, because they decrease the yield without increasing purity.

The pH is preferably kept at around 2, and must not exceed 3 in order not to reduce the yield (as occurs for example if sodium sulphite is used instead of the bisulphite) because high pH values favour substitution of the mobile Cl of the 1-chloro-2,6-dinitro-4-(trifluoromethyl)benzene. On the other hand, pH values which are too low favour $SO_2$ elimination, and thus make the treatment ineffective. In this respect, the initial DINI- TRO-PCBT must not contain mineral acids (such as $H_2SO_4$ or $HNO_3$), which can be eliminated by neutralisation.

The temperature is preferably kept at 70°–75° C. In this respect it is important not to fall below the melting point of the DINITRO-PCBT whereas too high temperatures favour yield reduction.

The reaction time is preferably 2 hours. Very long reaction times favour yield reduction.

The choice of the alkali for eliminating the acidity and last traces of the bisulphite-contaminated solution contained in the treated organic DINITRO-PCBT layer is not very important. $Na_2SO_3$ is preferably used for economical reasons and because the pH of the aqueous solution is not too high, so that there is no appreciable yield reduction.

DESCRIPTION OF THE PREFERRED EMBODIMENTS

Some examples of how the process according to the invention can be carried out in practice are given hereinafter. These are obviously purely indicative, and in no way limit the invention.

EXAMPLE 1

200 ml of $H_2O$ and 100 g of 1-chloro-2,6-dinitro-4-(trifluoromethyl)benzene (DINITRO-PCBT) are fed into a reactor. The mass is heated to 70°–75° C. under strong stirring in order to obtain perfect mixing of the organic layer with the aqueous layer, after which 13.3 g of a sodium bisulphite solution containing 25.5% of $SO_2$ (corresponding to an overall concentration of 1.59% if the $H_2O$ present in the mass is taken into account) are dripped in over about 20 minutes.

The mass is kept at 70°–75° C. for 2 hours under continuous vigorous stirring. The stirring is stopped, and the mass allowed to decant. The lower organic layer is separated, and is added to a solution containing 200 ml of $H_2O$ and 5 g of $Na_2CO_3$ which has previously been heated to 70°–75° C. The mass is stirred vigorously for 30–60 minutes, after which stirring is stopped.

The lower organic layer is separated, to give 96 g of purified DINITRO-PCBT.

The following results are obtained on converting samples of the initial DINITRO-PCBT and of the purified DINITRO-PCBT into TRIFLURALIN and analysing the products obtained for nitrosoamine:

using the initial DINITRO-PCBT 156 ppm NDPA present in the TRIFLURALIN produced;
using purified DINITRO-PCBT 0.5 ppm NDPA present in the TRIFLURALIN produced.

As can be seen, the NDPA content of the TRIFLURALIN produced using the DINITRO-PCBT prepared by the process according to the present invention is extremely low, and equal to one half the maximum allowable value under the most severe present legislation.

EXAMPLE 2

The procedure of Example 1 is followed, but using 26.6 g of a sodium bisulphite solution containing 25.5% of $SO_2$.

In this manner, 93 g of purified DINITRO-PCBT are obtained.

The NDPA content of the TRIFLURALIN produced is 0.45 ppm in this case.

EXAMPLE 3

The procedure of Example 1 is followed, but using 6.4 g of potassium metabisulphite containing 53% of $SO_2$ dissolved in 10 ml of $H_2O$.

95 g of purified DINITRO-PCBT are obtained.

The NDPA content of the TRIFLURALIN produced is 0.7 ppm.

EXAMPLE 4

The procedure of Example 1 is followed, but 3.3 g of sodium sulphite dissolved in 10 ml of $H_2O$ are used.

87 g of purified DINITRO-PCBT are obtained.

In this case, the too high pH value leads to an unacceptable yield reduction.

EXAMPLE 5

The procedure of Example 1 is followed, but using 6.1 g of a sodium bisulphite solution containing 25.5% of $SO_2$.

97 g of purified DINITRO-PCBT are obtained.

The NDPA content of the TRIFLURALIN produced is 0.9 ppm.

EXAMPLE 6

The procedure of Example 1 is followed, but using 8 g of 30% NaOH for the alkalising stage.

88 g of DINITRO-PCBT are obtained.

Again, the too high pH value leads to an unacceptable yield reduction.

I claim:

1. A process for removing nitrosating agents from 1-chloro-2,6-dinitro-4-(trifluoromethyl)benzene (DINITRO-PCBT), characterised in that DINITRO-PCBT is treated with an aqueous bisulphite solution having an $SO_2$ concentration of between 1% and 5% at a pH of between 1 and 3, at a temperature of between 50° and 100° C. for a time of between 1 and 3 hours, and in that the organic layer is separated from the aqueous layer, and the acidity and last traces of the bisulphite solution are eliminated from the organic layer by an aqueous alkaline solution.

2. A process as in claim 1, wherein sodium bisulphite is used for the DINITRO-PCBT treatment solution.

3. A process as in claim 1, wherein potassium or ammonium bisulphite are used for the DINITRO-PCBT treatment solution.

4. A process as in claim 1, wherein the bisulphite for treating the DINITRO-PCBT is prepared directly in the reactor by reacting $SO_2$ with alkali.

5. A process as in claim 1, wherein the aqueous bisulphite solution has an $SO_2$ concentration of 1.6%.

6. A process as in claim 1, wherein the pH is kept at around 2.

7. A process as in claim 1, wherein the temperature is kept between 70° and 75° C.

8. A process as in claim 1, wherein the reaction time is kept equal to about 2 hours.

9. A process as in claim 1, wherein sodium carbonate is used to form the alkaline solution for neutralising the organic layer.

* * * * *